(12) United States Patent
Qi et al.

(10) Patent No.: US 10,825,179 B2
(45) Date of Patent: Nov. 3, 2020

(54) METHOD FOR ESTABLISHING BIOMIMETIC NERVE GRAFT MODEL FOR NERVE FASCICLES OF EXTREMITIES

(71) Applicants: THE FIRST AFFILIATED HOSPITAL OF SUN YAT-SEN UNIVERSITY, Guangdong (CN); SCHOOL OF DATA AND COMPUTER SCIENCE OF SUN YAT-SEN UNIVERSITY, Guangdong (CN)

(72) Inventors: Jian Qi, Guangdong (CN); Qingtang Zhu, Guangdong (CN); Liwei Yan, Guangdong (CN); Zhi Yao, Guangdong (CN); Xiaolin Liu, Guangdong (CN); Yao Lu, Guangdong (CN); Shouliang Liu, Guangdong (CN); Tao Wang, Guangdong (CN); Tao Lin, Guangdong (CN)

(73) Assignees: THE FIRST AFFILIATED HOSPITAL OF SUN YAT-SEN UNIVERSITY, Guangzhou (CN); SCHOOL OF DATA AND COMPUTER SCIENCE OF SUN YAT-SEN UNIVERSITY, Guangzhou (CN)

( * ) Notice: Subject to any disclaimer, the term of this patent is extended or adjusted under 35 U.S.C. 154(b) by 60 days.

(21) Appl. No.: 16/246,544

(22) Filed: Jan. 13, 2019

(65) Prior Publication Data
US 2020/0027213 A1    Jan. 23, 2020

Related U.S. Application Data

(63) Continuation of application No. PCT/CN2018/096129, filed on Jul. 18, 2018.

(51) Int. Cl.
G06T 7/00 (2017.01)
G16H 30/40 (2018.01)
(Continued)

(52) U.S. Cl.
CPC .............. G06T 7/0016 (2013.01); G06T 7/62 (2017.01); G06T 19/20 (2013.01); G16H 30/40 (2018.01);
(Continued)

(58) Field of Classification Search
CPC ......... G06T 7/0016; G06T 7/62; G06T 19/20; G06T 2207/10081; G06T 2207/10088;
(Continued)

(56) References Cited

U.S. PATENT DOCUMENTS 9,278,120 B2 * 3/2016 Cruzat ................. A61K 31/569
9,820,747 B2 * 11/2017 Siemionow ........ A61B 17/1128
(Continued)

*Primary Examiner* — Ali Bayat

(57) ABSTRACT

The present invention provides a method for establishing a biomimetic nerve graft model for nerve fascicles of the extremities, which comprises the steps of: establishing a database of fascicles structures from nerve fascicles of the extremities with an imaging technique; obtaining information of a defective nerve trunk to be repaired of the extremities; and matching and fitting the information of the defective nerve trunk to be repaired of the extremities with/to the data in the database of fascicles structures, to establish a biomimetic nerve graft model that conforms to the characteristics of fascicles microstructure for nerve fascicles of the defective nerve trunk. In the present invention, the imaging technique and clinical data are fully utilized, to establish a biomimetic nerve graft model conforming to the characteristics of fascicles microstructure for varying types of detects, thus providing more accurate model information for repair of nerve trunk defects in the extremities.

4 Claims, 4 Drawing Sheets

(51) Int. Cl.
*G06T 7/62* (2017.01)
*G06T 19/20* (2011.01)

(52) U.S. Cl.
CPC ............... *G06T 2207/10081* (2013.01); *G06T 2207/10088* (2013.01); *G06T 2219/2021* (2013.01)

(58) Field of Classification Search
CPC ............ G06T 2219/2021; G16H 30/40; A61L 2300/412; A61L 2430/32
USPC ........................................................ 382/131
See application file for complete search history.

(56) References Cited

U.S. PATENT DOCUMENTS

| | | | |
|---|---|---|---|
| 10,363,041 B2 * | 7/2019 | Yu | C08L 67/04 |
| 2003/0040112 A1 * | 2/2003 | Muir | A61K 35/30 |
| | | | 435/368 |
| 2010/0291180 A1 * | 11/2010 | Uhrich | A61L 27/227 |
| | | | 424/426 |
| 2011/0087338 A1 * | 4/2011 | Siemionow | A61B 17/1128 |
| | | | 623/23.72 |
| 2013/0190687 A1 * | 7/2013 | Kokai | A61L 27/58 |
| | | | 604/93.01 |
| 2013/0304174 A1 * | 11/2013 | Langhals | A61F 2/0811 |
| | | | 607/118 |
| 2019/0235039 A1 * | 8/2019 | Zhu | G01R 33/543 |
| 2019/0262500 A1 * | 8/2019 | Xu | A61L 27/56 |
| 2019/0328393 A1 * | 10/2019 | Yu | A61L 27/18 |

* cited by examiner

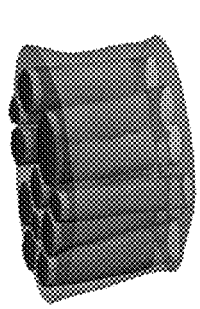 
FIG.4A    FIG.4B
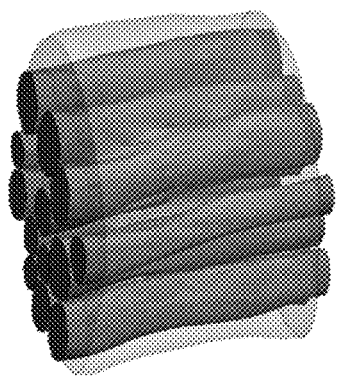 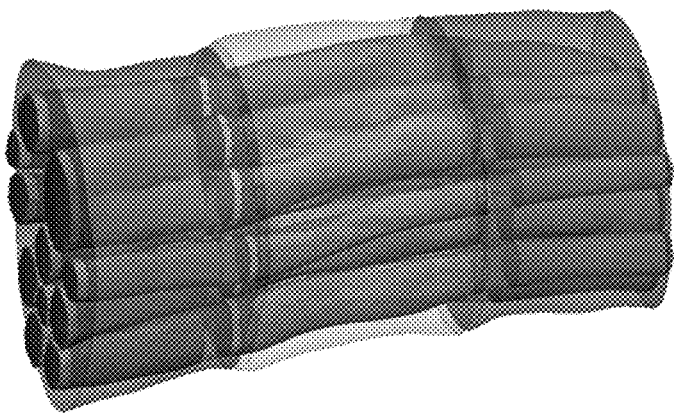
FIG.4C    FIG.4D
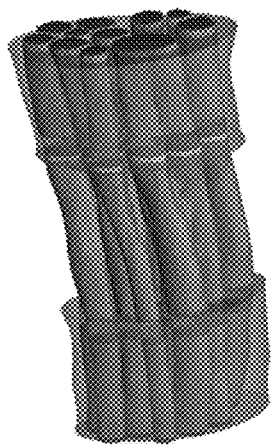 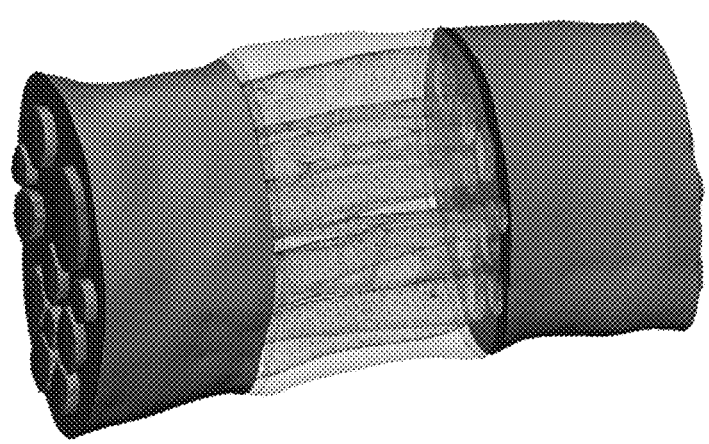
FIG.4E    FIG.4F

METHOD FOR ESTABLISHING BIOMIMETIC NERVE GRAFT MODEL FOR NERVE FASCICLES OF EXTREMITIES

CROSS REFERENCE TO RELATED APPLICATIONS

The present application is a Continuation Application of PCT Application No. PCT/CN2018/096129 filed on Jul. 18, 2018, the contents of which are hereby incorporated by reference.

TECHNICAL FIELD

The present invention relates to the technical filed of clinical application of repairing of nerve defects, and particularly to a method for establishing a biomimetic nerve graft model for nerve fascicles of the extremities.

BACKGROUND

Peripheral nerve defects are common clinical diseases, particularly the defects in the extremities will lead to severe physical disability and bring about a huge social burden. At present, the gold-standard autologous nerve for clinical treatment is limited in the source, and defects, such as functional damage in the donor area, exist. There is an urgent need in neurosurgery to develop a nerve graft that can replace autologous nerve transplantation. Existing biomaterials for repairing peripheral nerve defects mainly include nerve conduits and decellularized nerve grafts prepared with synthetic or natural materials. However, in practical clinical work, because the site of the patient's defective injury, the size of the nerve, and the condition of the nerve branches in the proximal and distal segments vary greatly, there is no good technical means and technical reserves available to specifically design and biofabricate fascicles grafts for the varying types of injuries.

The construction of biomaterials by means of biofabrication has attracted much attention in recent years. The main advantage is that the structure of the biomaterials has the optimal structural distribution of biological evolution to achieve the biological functions. It is found in the study of peripheral nerve structure that changing the matching degree of nerve fascicles in autologous nerve grafts alone will produce an impact on the nerve regeneration, which proves that the physical guidance in configuration of nerve fascicles plays an important role. With the rise of the concept of precision medicine and the rapid development of biofabrication technologies, the latest research also attempts to achieve structure biomimetics by using biofabrication technologies. However, there is no good system available for designing nerve grafts. The structural matching at present still remains at the level of nerve trunk. The matching at the level of nerve fascicles largely depends merely on imagination. Therefore, to further study the design of fascicles grafts for peripheral nerves, the primary problem to be solved is to fully understand the cross-fusion rule of nerve fascicles on the basis of large quantities of data.

The study on the internal structure of the peripheral nerves has been undergoing for decades, and the research level has been deepened increasingly from the general anatomy of the peripheral nerves to the nerve fascicles and then to the endoneurium. The research methods have also evolved from the traditional histological staining and sections to modern imaging techniques with the continuous development of information technology. Three-dimensional visualization and holographic imaging techniques have also made the neuroscience research more systematic and accurate. In recent years, the new advances in the emerging medical imaging technologies such as Micro-CT and Micro-MRI have brought new ideas for technological breakthroughs in the study of neural structures. The nerve is pretreated with an iodine reagent combined with freeze-drying, and high-precision two-dimensional images of the interior of peripheral nerves are obtained by Micro-CT. Consecutively scanned two-dimensional images that conform to the segmentation and reconstruction of nerve fascicles can also be obtained with the peripheral nerve by performing Micro-MRI with Ti weighted sequence in a scanning environment of a gadolinium reagent. The Minimally Invasive Hand Surgery Team of the First Affiliated Hospital of Sun Yat-sen University carried out the multi-regional and multi-level scanning of ex-vivo samples with the support of a number of research funds, and obtained a three-dimensional reconstruction model of the fascicles structure for peripheral nerve, from which the changes in spatial position and distribution of peripheral nerve fascicles in a three-dimensional configuration can be observed. Referring to FIG. 1, observation for the distributions of nerve fascicles is carried out with the imagines captured respectively from the distal, middle and proximal sections of the three-dimensional reconstruction model, and it is recognized that a nerve fascicle may have a large change in the spatial position at a short distance. The complex and varying configuration of the nerve fascicle in three-dimensional space is a key point and difficulty in designing and biofabrication of the fascicles grafts. At present, it is unable to establish a biomimetic nerve graft model that conforms to the characteristics of fascicles microstructure for varying types of injuries.

SUMMARY

Technical Problem

To solve the above problems, the present invention provides a method for establishing a biomimetic nerve graft model for nerve fascicles of the extremities, in which the imaging techniques and clinical data are fully utilized, to establish a biomimetic nerve graft model conforming to the characteristics of fascicles microstructure for varying types of injuries, thus providing more accurate model information for the repair of nerve trunk defects in the extremities.

The present invention provides a method for establishing a biomimetic nerve graft model for nerve fascicles of the extremities, which comprises the steps of:

S1: establishing a database of fascicles structures from nerve fascicles of the extremities with an imaging technique;

S2: obtaining information of a defective nerve trunk to be repaired of the extremities; and S3: matching and fitting the information of the defective nerve trunk to be repaired of the extremities with/to the data in the database of fascicles structures, to establish a biomimetic nerve graft model that conforms to the characteristics of fascicles microstructure for nerve fascicles of the defective nerve trunk.

Preferably, Step S1 comprises the following steps:

obtaining ex-vivo nerve samples from nerve fascicles of the extremities;

obtaining two-dimensional image data of each of the ex-vivo nerve samples by Micro-CT and/or Micro-MRI; and obtaining a three-dimensional reconstruction model for each of the ex-vivo nerve samples by using the two-dimensional image data, storing, and thereby establishing the database of fascicles structures.

Preferably, the ex-vivo nerve sample is taken from one or more of upper limb nerves below the axillary plane, including the median nerve, radial nerve, ulnar nerve, and musculocutaneous nerve; and lower limb nerves below the inguinal plane, including the femoral nerve, sciatic nerve, tibial nerve and common peroneal nerve.

Preferably, the two-dimensional image data includes consecutively scanned images of cross sections, sagittal planes, and/or coronal sections of each of the ex-vivo nerve samples.

Preferably, Step S2 comprises the following steps:
determining the type and time of injury of the patient, and preliminarily locating the target injured nerve;
scanning the gross forms of nerve trunks respectively on both healthy side and affected side of the patient, and obtaining a scanned image of a defect area on the affected side and a scanned image of a normal area on the healthy normal side corresponding to the defect area; and
comparing and analyzing the scanned image of the defect area on the affected side with the scanned image of the normal area on the healthy side to determine the type, spatial position, length, and nerve branching of the nerve trunk in the defect area, and measuring the diameter and length of the nerve trunk in the defect area, such that the information of a defective nerve trunk is obtained.

Preferably, Step S3 comprises the following steps:
according to the information of the defective nerve trunk to be repaired of the extremities, searching the database of fascicles structures to find out a segment of nerve having a fascicles structure with a type, spatial position, length, and branching of the nerve matching those of the defective nerve, and extracting the spatial structure data of the fascicles structure of the segment;
fitting data in the information of the defective nerve trunk to be repaired to the spatial structure data extracted from the database, and establishing a rough three-dimensional model with the fitted data;
adjusting the established three-dimensional model according to the general nerve morphology, the nerve branching, and the three-dimensional spatial position distribution of nerve fascicles at both proximal and distal ends of the nerve trunk in the defect area;
modifying the form, curvature and smoothness of the adjusted three-dimensional model;
matching the modified three-dimensional model with the proximal and distal ends of the nerve trunk in the defect area with respect to the general nerve morphology, the nerve branching, and the three-dimensional spatial position distribution of nerve fascicles;
if a parameter for evaluating the degree of matching is less than a preset value, repeating the fitting, adjusting, modifying, and matching steps until the parameter for evaluating the degree of matching reaches or exceeds the preset value; and
if the parameter for evaluating the degree of matching is equal to or greater than the preset value, taking the matched three-dimensional model as a biomimetic nerve graft model for the nerve in the defect area.

BRIEF DESCRIPTION OF THE DRAWINGS

FIGS. 4A-4F show an embodiment of establishing a biomimetic nerve graft model conforming to the characteristics of fascicles microstructure based on a database of fascicles structures.

DESCRIPTION OF THE EMBODIMENTS

To make the technical problems to be solved, the technical solutions and advantageous effects of the present invention more clearly, the present invention will be described in further detail below with reference to the accompanying drawings and embodiments. It is to be understood that the specific embodiments described herein are merely illustrative of and are not intended to limit the present invention.

Figure 1:
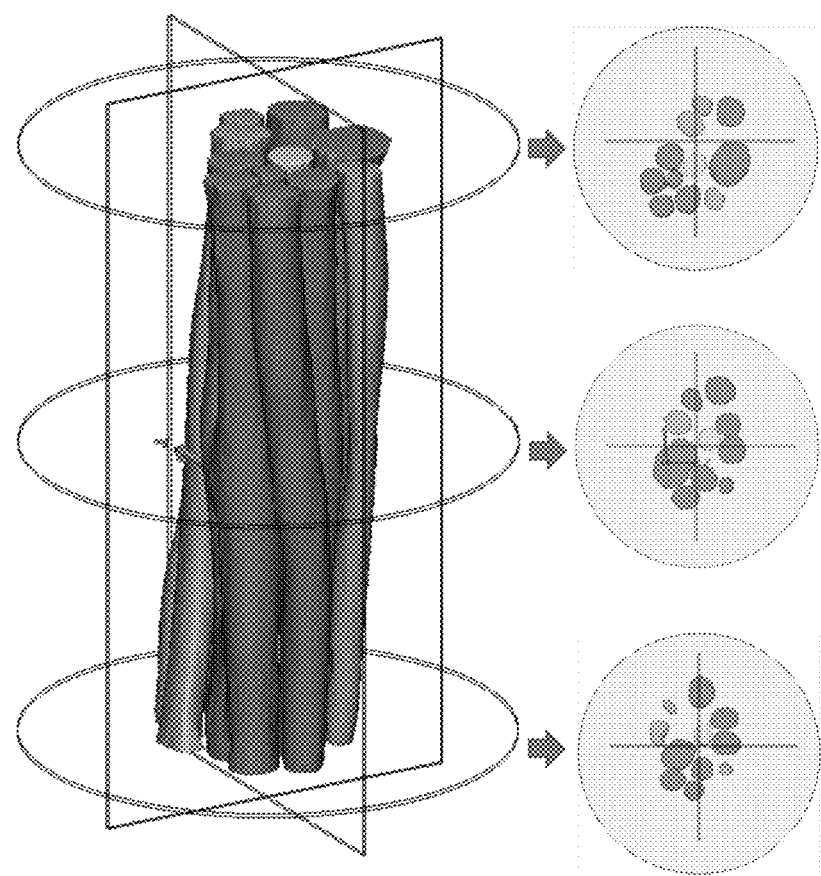
FIG. 1 shows a three-dimensional model of fascicles structures in peripheral nerves established in conjunction with an imaging technique.
Figure 2:
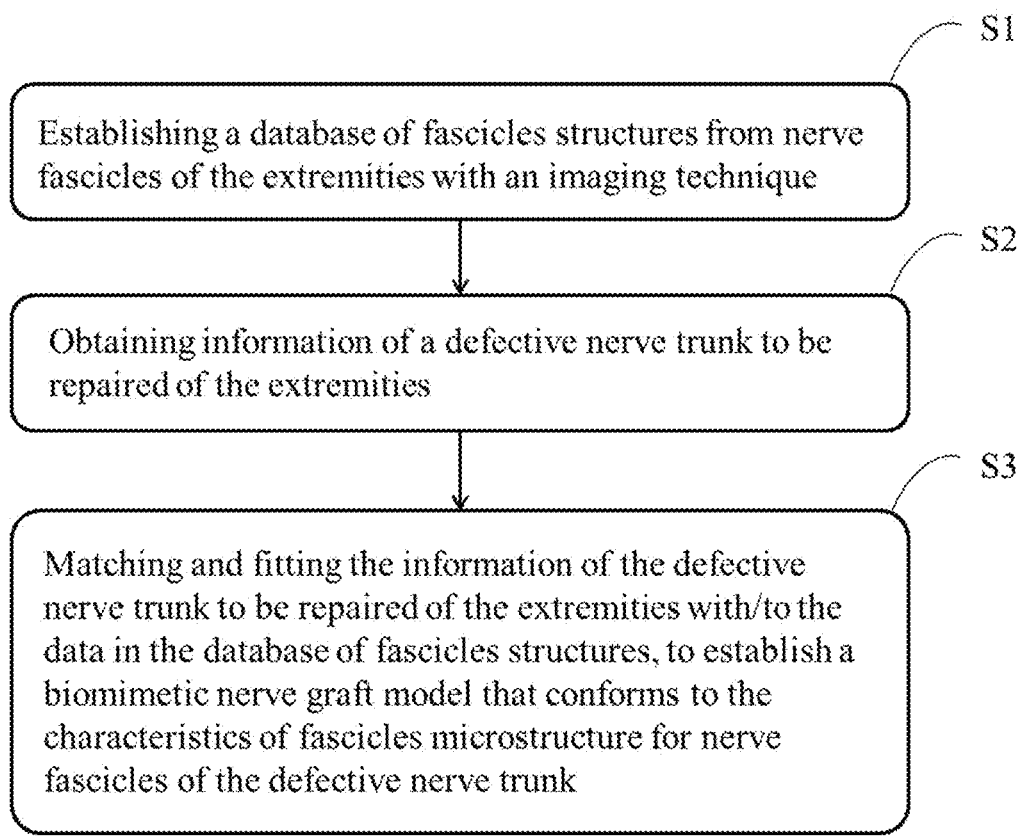
FIG. 2 shows a main flow chart of a method for establishing a biomimetic nerve graft model for nerve fascicles of the extremities according to an embodiment of the present invention.

FIG. 2 shows a main flow chart of a method for establishing a biomimetic nerve graft model for nerve fascicles of the extremities according to an embodiment of the present invention, which comprises mainly the following steps:

S1: establishing a database of fascicles structures from nerve fascicles of the extremities with an imaging technique;

S2: obtaining information of a defective nerve trunk to be repaired of the extremities; and S3: matching and fitting the information of the defective nerve trunk to be repaired of the extremities with/to the data in the database of fascicles structures, to establish a biomimetic nerve graft model that conforms to the characteristics of fascicles microstructure for nerve fascicles of the defective nerve trunk.

Particularly, the method of this embodiment comprises specifically the following steps.

(1) Establish a database of fascicles structures from nerve fascicles of the extremities with an imaging technique.

Ex-vivo nerve samples from nerve fascicles of the extremities are obtained. The nerves are obtained within 2 hours after ligation of the major vessel of the amputated limb specimen, including upper limb nerves below the axillary plane and lower limb nerves below the inguinal plane. The upper limb nerves include the median nerve, radial nerve, ulnar nerve, and musculocutaneous nerve. The lower limb nerves include the femoral nerve, sciatic nerve, tibial nerve and common peroneal nerve. The obtained nerves are immediately fixed in 4% paraformaldehyde, and prepared into ex-vivo nerve samples for scanning. At least 3 samples are taken for scanning for each segment of each type of nerves.

Figure 3A:
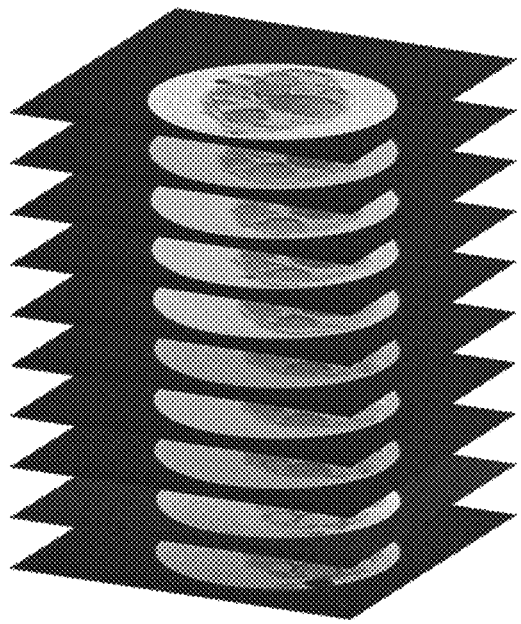
FIGS. 3A-3F show Micro-MRI scanned images of nerve fascicles and three-dimensional reconstruction thereof according to some embodiments.
Figure 3B:
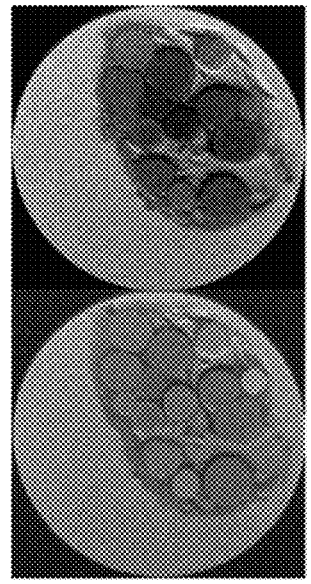
Figure 3C:
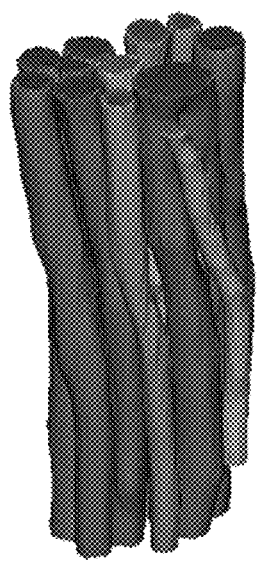
Figure 3D:
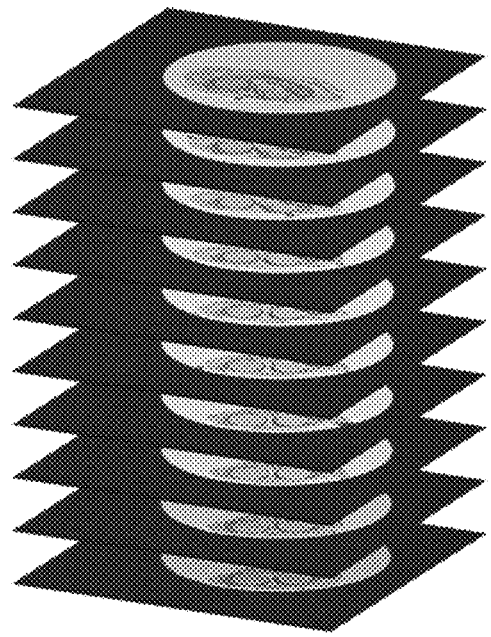

Two-dimensional image data of each of the ex-vivo nerve samples is obtained by an imaging technique. The imaging technique herein includes Micro-CT and/or Micro-MRI. The scanning parameters of Micro-CT and/or Micro-MRI are set, and the pre-treated ex-vivo nerve samples are scanned to obtain the two-dimensional image data. Preferably, the two-dimensional image data includes consecutively scanned images of cross sections, sagittal planes, and/or coronal sections of each of the ex-vivo nerve samples. FIGS. 3A and 3D illustratively show consecutively scanned two-dimensional images of the cross sections of the ex-vivo nerve samples of the tibial nerve and the common peroneal nerve obtained by Micro-MRI, respectively.

Figure 3E:
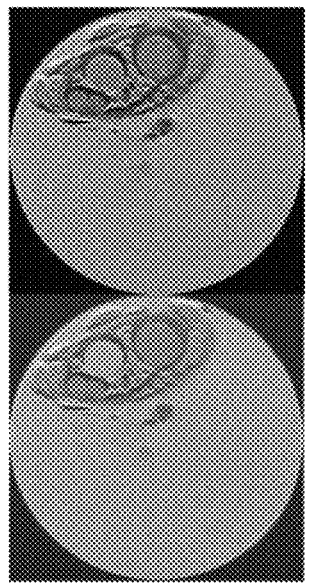
Figure 3F:
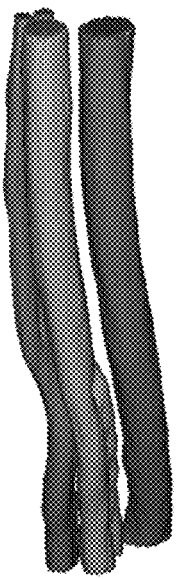

Three-dimensional reconstruction of fascicles structures in nerves is performed to establish a database of fascicles structures. The two-dimensional image data obtained in the above steps is segmented using a three-dimensional reconstruction software to extract the nerve fascicles (FIGS. 3B and 3E illustratively show the segmentation of the nerve fascicles in the two-dimensional images of the tibial nerve and the common peroneal nerve respectively), the topological structure of the nerve fascicles is presented by visualization, and three-dimensional reconstruction of each of the ex-vivo nerve samples is performed, to obtain a three-dimensional reconstruction model presenting the configuration of the fascicles structure in each type of nerve (FIGS. 3C and 3F illustratively show the fascicles structure in the tibial nerve and the common peroneal nerve after three-dimensional reconstruction), and then to store it. In this way, the database of the fascicles structures is established.

(2) Obtain information of a defective nerve trunk to be repaired of the extremities.

The type and time of injury of the patient are determined, and the target injured nerve is preliminarily located.

The gross forms of nerve trunks respectively on both healthy side and affected side of the patient are scanned by preferably high-precision MRI, and a scanned image of a defect area on the affected side and a scanned image of a normal area on the healthy side corresponding to the defect area are obtained.

The scanned image of the defect area on the affected side and the scanned image of the normal area on the healthy side are compared and analyzed to determine the type, spatial position, length, and nerve branching of the nerve trunk in the defect area, and the diameter and length of the nerve trunk in the defect area are measured. In this way, the information of the defective nerve trunk to be repaired is obtained.

(3) Match and fit the information of the defective nerve trunk to be repaired of the extremities with/to the data in the database of fascicles structures, to establish a biomimetic nerve graft model that conforms to the characteristics of fascicles microstructure for nerve fascicles of the defective nerve trunk.

On the basis of the type, spatial position, and length of the nerve trunk in the defect area determined in the above step, the database of fascicles structures is searched to find out a segment of nerve having a fascicles structure with a type, spatial position, length, and nerve branching matching those of the defective nerve, and the spatial structure data of the fascicles structure of the segment is extracted.

The measured data of the detect area obtained in the above step is fitted to the spatial structure data extracted from the database, and a rough three-dimensional model is established with the fitted data.

The established three-dimensional model is adjusted according to the general nerve morphology, the nerve branching, and the three-dimensional spatial position distribution of nerve fascicles at both proximal and distal ends of the nerve trunk in the defect area.

The form, curvature and smoothness of the adjusted three-dimensional model are modified using three-dimensional model software.

The modified three-dimensional model is matched with the proximal and distal ends of the nerve trunk in the defect area with respect to the general nerve morphology, the nerve branching, and the three-dimensional spatial position distribution of nerve fascicles.

If a parameter for evaluating the degree of matching is less than a preset value, the fitting, adjusting, modifying, and matching steps are repeated until the parameter for evaluating the degree of matching reaches or exceeds the preset value.

If the parameter for evaluating the degree of matching is greater than or equal to the preset value, the matched three-dimensional model is taken as a biomimetic nerve graft model for the nerve in the defect area.

FIGS. 4A-4F illustratively show an embodiment of establishing a biomimetic nerve graft model conforming to the characteristics of fascicles microstructure based on a database of fascicles structures. FIGS. 4A and 4B show the proximal and distal ends of the nerve trunk in the defect area. The fascicles structures in the proximal and distal ends and the difference therebetween can be clearly identified from FIG. 4B. FIG. 4C is an established three-dimensional model for the nerve trunk in the defect area. FIGS. 4D to 4F show the matching of the established three-dimensional model to the proximal and distal ends of the nerve trunk in the defect area.

The above description is merely preferred specific embodiments of the present invention, and the scope of the present invention is not limited thereto. Simple variations of or equivalent substitutions to the resulting technical solutions made by any person skilled in the art without creative efforts and without departing from the technical scope disclosed herein are within the scope of the present invention.

What is claimed is:

1. A method for establishing a biomimetic nerve graft model for nerve fascicles of the extremities, comprising the steps of:
    S1: establishing a database of fascicles structures from nerve fascicles of the extremities with an imaging technique;
    S2: obtaining information of a defective nerve trunk to be repaired of the extremities; and
    S3: matching and fitting the information of the defective nerve trunk to be repaired of the extremities with/to the data in the database of fascicles structures, to establish a biomimetic nerve graft model that conforms to the characteristics of fascicles microstructure for nerve fascicles of the defective nerve trunk;
    wherein Step S1 comprises the following steps:
    obtaining ex-vivo nerve samples from nerve fascicles of the extremities;
    obtaining two-dimensional image data of each of the ex-vivo nerve samples by Micro-CT and/or Micro-MRI; and
    obtaining a three-dimensional reconstruction model for each of the ex-vivo nerve samples by using the two-dimensional image data, storing, and thereby establishing the database of fascicles structures; and
    wherein the ex-vivo nerve sample is taken from one or more of upper limb nerves below the axillary plane, including the median nerve, radial nerve, ulnar nerve, and musculocutaneous nerve; and lower limb nerves below the inguinal plane, including the femoral nerve, sciatic nerve, tibial nerve and common peroneal nerve.

2. The method for establishing a biomimetic nerve graft model for nerve fascicles of the extremities according to claim 1, wherein the two-dimensional image data includes consecutively scanned images of cross sections, sagittal planes, and/or coronal sections of each of the ex-vivo nerve samples.

3. The method for establishing a biomimetic nerve graft model for nerve fascicles of the extremities according to claim 1, wherein Step S2 comprises the following steps:
    determining the type and time of injury of the patient, and preliminarily locating the target injured nerve;

scanning the gross forms of nerve trunks respectively on both healthy side and affected side of the patient, and obtaining a scanned image of a defect area on the affected side and a scanned image of a normal area on the healthy side corresponding to the defect area; and comparing and analyzing the scanned image of the defect area on the affected side and the scanned image of the normal area on the healthy side to determine the type, spatial position, length, and nerve branching of the nerve trunk in the defect area, and measuring the diameter and length of the nerve trunk in the defect area, such that the information of the defective nerve trunk to be repaired is obtained.

4. The method for establishing a biomimetic nerve graft model for nerve fascicles of the extremities according to claim 3, wherein Step S3 comprises the following steps:

according to the information of the defective nerve trunk to be repaired, searching the database of fascicles structures to find out a segment of nerve having a fascicles structure with a type, spatial position, length, and nerve branching of the nerve matching those of the defective nerve, and extracting the spatial structure data of the fascicles structure of the segment;

fitting data in the information of the defective nerve trunk to be repaired to the spatial structure data extracted from the database, and establishing a rough three-dimensional model with the fitted data;

adjusting the established three-dimensional model according to the general nerve morphology, the nerve branching, and the three-dimensional spatial position distribution of nerve fascicles at both proximal and distal ends of the nerve trunk in the defect area;

modifying the form, curvature and smoothness of the adjusted three-dimensional model;

matching the modified three-dimensional model with the proximal and distal ends of the nerve trunk in the defect area with respect to the general nerve morphology, the nerve branching, and the three-dimensional spatial position distribution of nerve fascicles;

if a parameter for evaluating the degree of matching is less than a preset value, repeating the fitting, adjusting, modifying, and matching steps until the parameter for evaluating the degree of matching reaches or exceeds the preset value; and if the parameter for evaluating the degree of matching is equal to or greater than the preset value, taking the matched three-dimensional model as a biomimetic nerve graft model for the nerve in the defect area.

* * * * *